(12) United States Patent
Ji

(10) Patent No.: US 9,157,762 B2
(45) Date of Patent: Oct. 13, 2015

(54) METHOD AND APPARATUS FOR DIRECTIONAL CALIBRATION AND TRACKING

(71) Applicant: Ying Ji, Wuxi (CN)

(72) Inventor: Ying Ji, Wuxi (CN)

(*) Notice: Subject to any disclaimer, the term of this patent is extended or adjusted under 35 U.S.C. 154(b) by 0 days.

(21) Appl. No.: 14/250,353

(22) Filed: Apr. 10, 2014

(65) Prior Publication Data
US 2014/0214358 A1 Jul. 31, 2014

Related U.S. Application Data

(63) Continuation of application No. PCT/CN2011/080636, filed on Oct. 11, 2011.

(51) Int. Cl.
| | |
|---|---|
| G06F 17/40 | (2006.01) |
| G06F 19/00 | (2011.01) |
| G01C 25/00 | (2006.01) |
| A61B 19/00 | (2006.01) |
| G01C 21/20 | (2006.01) |
| A61B 17/00 | (2006.01) |

(52) U.S. Cl.
CPC .......... *G01C 25/00* (2013.01); *A61B 19/5244* (2013.01); *G01C 21/20* (2013.01); *A61B 2017/00725* (2013.01); *G06F 17/40* (2013.01); *G06F 19/00* (2013.01)

(58) Field of Classification Search
None
See application file for complete search history.

(56) References Cited

U.S. PATENT DOCUMENTS

| 6,594,600 B1 * | 7/2003 | Arnoul et al. ............. 702/94 |
| 2009/0099445 A1 * | 4/2009 | Burger .................... 600/424 |

* cited by examiner

*Primary Examiner* — Edward Cosimano
(74) *Attorney, Agent, or Firm* — Syncoda LLC; Feng Ma

(57) ABSTRACT

Method and apparatus are provided to determine directional calibration parameters of an object. A method includes: disposing a tracking marker to the object, disposing the object on a calibration tool, rotating the object around its set linear axis while keeping the set linear direction unchanged, determining at least two three-dimensional rotation matrices of the tracking marker via a position tracking apparatus, and using the three-dimensional rotation matrices to determine the directional calibration parameters with the formula of two-point position relationship or rectilinear direction rotation relationship in the three-dimensional space. The action direction of the object is determined based on the determined directional calibration parameters and the current three-dimensional rotation matrix of the tracking marker. Without placing the object in a known direction or determining two points on the direction, the disclosed methods provide convenient ways to determine the directional calibration parameters, and to determine the action direction of the object.

23 Claims, 5 Drawing Sheets

Mounting a tracking marker on the object, in a way such that the relative direction or angle in the three-dimensional space between the direction of the straight line for the object and the tracking marker is the same as the relative direction or angel in the three-dimensional space between the direction of the straight line for the object and the tracking marker during the determination of the directional calibration parameters, and disposing the tracking marker in a traceable region for a position tracking apparatus;

↓

During tracking, obtaining the rotation status parameters of the tracking marker in the three-dimensional space via the position tracking apparatus to determine the three-dimensional rotation matrix;

↓

Based on the three-dimensional rotation matrix determined above, computing the action direction of the object.

Fig. 6

METHOD AND APPARATUS FOR DIRECTIONAL CALIBRATION AND TRACKING

CROSS-REFERENCE TO RELATED APPLICATIONS

The present application is a continuation of, and claims priority to, PCT/CN2011/080636, filed Oct. 11, 2011, the disclosure of which is hereby incorporated by reference in its entirety.

BACKGROUND

In many areas, such as in medical applications, an object's spatial position and direction may be measured while the object moves around in a three-dimensional space. A position tracking apparatus may be used to detect the object's movement directions and positions.

SUMMARY

The present disclosure relates to methods in position tracking systems to determine the directional calibration parameters and the action direction of an object to be tracked, and relates to the calibration tool used in the methods of determining the directional calibration parameters.

Specifically, methods and apparatus for accurately determining directional calibration parameters and directions of movement of an object to be tracked.

In some embodiments, a method of determining the directional calibration parameters of an object to be tracked or measured may comprise:

a) disposing a tracking marker over an object to be tracked, then placing the object on a calibration tool, and having the tracking marker in a traceable region for a position tracking apparatus;

b) with the aid of the calibration tool, rotating the object around a set straight line as an axis, while keeping the direction of the straight line unchanged in the three-dimensional space;

c) during rotation of the object, obtaining at least two groups of rotation status parameters of the tracking marker in at least two different rotation positions via the position tracking apparatus; from the groups of rotation status parameters, determining at least two three-dimensional rotation matrices for computing directional calibration parameters;

d) with at least two three-dimensional rotation matrices determined from step c), solving simultaneous equations to compute the directional calibration parameters for the set direction of the object.

Some implementations to compute the directional calibration parameters in step d) include:

Setting point A and point B on the set straight line with a distance D apart (D is larger than 0); setting point O at the tracking marker's center to represent the tracking marker; setting three-dimensional coordinates A ($X_A$, $Y_A$, $Z_A$), B ($X_B$, $Y_B$, $Z_B$) and C (Xc, Yc, Zc) respectively;

Substituting three-dimensional coordinates of point A, B and O into the formula of the two-point position relationship in the three-dimensional space to obtain equations 1)-6):

$$X_A = X_c + X_{AO} \times M_p(1,1) + Y_{AO} \times M_p(2,1) + Z_{AO} \times M_p(3,1) \quad \quad 1);$$

$$Y_A = Y_c + X_{AO} \times M_p(1,2) + Y_{AO} \times M_p(2,2) + Z_{AO} \times M_p(3,2) \quad \quad 2);$$

$$Z_A = Z_c + X_{AO} \times M_p(1,3) + Y_{AO} \times M_p(2,3) + Z_{AO} \times M_p(3,3) \quad \quad 3);$$

$$X_B = X_c + X_{BO} \times M_p(1,1) + Y_{BO} \times M_p(2,1) + Z_{BO} \times M_p(3,1) \quad \quad 4);$$

$$Y_B = Y_c + X_{BO} \times M_p(1,2) + Y_{BO} \times M_p(2,2) + Z_{BO} \times M_p(3,2) \quad \quad 5);$$

$$Z_B = Z_c + X_{BO} \times M_p(1,3) + Y_{BO} \times M_p(2,3) + Z_{BO} \times M_p(3,3) \quad \quad 6);$$

wherein $X_{AO}$, $Y_{AO}$, $Z_{AO}$ are offset distances between point A and Point O. $X_{BO}$, $Y_{BO}$, $Z_{BO}$ are offset distances between point B and Point O. The matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing directional calibration parameters determined from step c), p=1, 2, ..., n, where n is a positive integer greater than 1.

Setting $\delta x = X_A - X_B$, $\delta y = Y_A - Y_B$, $\delta z = Z_A - Z_B$, where $\delta x$, $\delta y$, $\delta z$ represent X, Y, Z components of the linear direction in three-dimensional coordinate system.

Equation 1)-Equation 4) results in Equation 7); Equation 2)-Equation 5) results in Equation 8); Equation 3)-Equation 6) results in Equation 9):

$$\delta x = X_{off} \times M_p(1,1) + Y_{off} \times M_p(2,1) + Z_{off} \times M_p(3,1) \quad \quad 7);$$

$$\delta y = X_{off} \times M_p(1,2) + Y_{off} \times M_p(2,2) + Z_{off} \times M_p(3,2) \quad \quad 8);$$

$$\delta z = X_{off} \times M_p(1,3) + Y_{off} \times M_p(2,3) + Z_{off} \times M_p(3,3) \quad \quad 9);$$

wherein $X_{off} = X_{AO} - X_{BO}$, $Y_{off} = Y_{AO} - Y_{BO}$, $Z_{off} = Z_{AO} - Z_{BO}$, $X_{off}$, $Y_{off}$, $Z_{off}$ are X, Y, Z components of directional calibration parameters for the set straight line for the object. The equations 7)-9) are the relationship equations for linear direction rotation.

To compute the directional calibration parameters $X_{off}$, $Y_{off}$, $Z_{off}$, an implementation is to use the formula for determining the distance between the two points, which is the following.

The formula of distance D between point A and point B is $$D = \sqrt{(X_A - X_B)^2 + (Y_A - Y_B)^2 + (Z_A - Z_B)^2};$$

or $$D = \sqrt{\delta x^2 + \delta y^2 + \delta z^2} \quad \quad 10);$$

wherein D is a number greater than 0; Substituting each three-dimensional rotation matrix for computing directional calibration parameters determined from step C) into equations 7)-9), plus equation 10), constitutes simultaneous equations; Solving the combined simultaneous equations gives $X_{off}$, $Y_{off}$, $Z_{off}$.

To compute the directional calibration parameters $X_{off}$, $Y_{off}$, $Z_{off}$, another implementation is to have one of the components of the direction be a non-zero constant, which is the following:

Among $\delta x$, $\delta y$, $\delta z$, setting a non-zero component as known non-zero constant; substituting each three-dimensional rotation matrix for computing directional calibration parameters determined from step c) into equations 7)-9), to obtain non-homogeneous linear equations; solving the non-homogeneous linear equations gives $X_{off}$, $Y_{off}$, $Z_{off}$.

In some embodiments, the calibration tool includes a chassis. A holding bracket is set on the chassis for holding the object mounted with a tracking marker. The holding bracket ensures that the direction of the straight line for the object remains unchanged in the three-dimensional space, while the object rotates around the set straight line as an axis.

In some embodiments, a method of determining the action direction of an object comprises:

a) disposing a tracking marker over an object, in a way that the relative direction or angle in the three-dimensional space between the direction of the set straight line for the object and the tracking marker is the same as the relative direction or angel in the three-dimensional space between the direction of the set straight line for the object and the tracking marker during the determination of the directional calibration parameters, and disposing the tracking marker in the traceable region for the position tracking apparatus.

b) during tracking, obtaining the rotation status parameters in the three-dimensional space of the tracking marker via the position tracking apparatus, in order to determine the three-dimensional rotation matrix $M_S$.

To compute the current direction, an implementation is to substitute $M_S$ and $X_{off}$, $Y_{off}$, $Z_{off}$ into equations 7)-9), giving:

$$\delta x\_s = X_{off} \times M_S(1,1) + Y_{off} \times M_S(2,1) + Z_{off} \times M_S(3,1) \quad 11);$$

$$\delta y\_s = X_{off} \times M_S(1,2) + Y_{off} \times M_S(2,2) + Z_{off} \times M_S(3,2) \quad 12);$$

$$\delta z\_s = X_{off} \times M_S(1,3) + Y_{off} \times M_S(2,3) + Z_{off} \times M_S(3,3) \quad 13);$$

where $\delta x\_s$, $\delta y\_s$, $\delta z\_s$ are X, Y, Z components of the current direction. Hence the current direction of the object is determined.

BRIEF DESCRIPTION OF THE DRAWINGS

FIG. 6 is a flowchart of one embodiment to determine the action direction for the object;

DETAILED DESCRIPTION

Described below are some embodiments of the methods of determining the directional calibration parameters and the action direction of an object, and a calibration tool used in the method of determining the directional calibration parameters.

In some applications, infrared tracking and/or electromagnetic tracking may be adopted. When an infrared tracking apparatus is used, one or more tracking markers may be mounted on the object to be tracked. The markers can emit infrared light (active mode), or reflect infrared light (passive mode). Through the computation over the transmission of the emitted/reflected infrared light, the infrared tracking apparatus can deduce the tracking markers' spatial positions and directions of movement. When an electromagnetic tracking apparatus is used, one or more tracking markers, for example, that contains sensing coils, can be mounted on the object to be tracked. Through the computation over the induced voltage on the sensing coil, the electromagnetic tracking apparatus can deduce the tracking markers' positions and directions of movement. By following the tracking markers' movement, the position tracking apparatus can provide information of the positions and directions of movement of the object in a real-time manner.

In some medical applications, for example, the direction of some surgical instruments may need to be controlled accurately during operation. The precise determination of the action direction of the surgical instrument can play an important role in the surgical outcome.

Applying a surgical navigation system is a good way to achieve a better accuracy for certain surgical procedures. The surgical navigation system includes position tracking apparatus, surgical navigation software, etc. The surgical navigation system can track a surgical instrument's movement in the three dimensional space and display an image of the surgical instrument's movement with respect to the anatomic image of the patient on a monitor. These images provide a visual tool to guide the procedure for surgeons.

Figure 1:
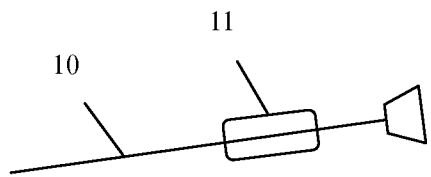
FIG. 1 is a schematic view of a tracking marker disposed over an object to be tracked or measured.

As shown in FIG. 1, in order to track the trajectory of the object 10, a tracking marker 11 is mounted on the object 10, so that the position and direction of the tracking marker can be tracked via the position tracking apparatus, and thereby the trajectory of the object 10 can be determined In practice, an object often has its distinctive geometric shape, which causes the tracking marker's spatial position and direction to represent only for itself, but not so much for the object. How to accurately indicate the action direction of the object via the direction of the tracking marker involves a calibration issue.

One approach for this issue is to initially place the object 10 at a known direction, measure the direction parameters of the tracking marker 11 from the position tracking apparatus, compute the deviation between the known direction of the object 10 and the direction of the tracking marker 11. The deviation is regarded as the directional calibration parameters. When the object 10 moves in any direction, based on the direction of the tracking marker 11 and by applying the previously determined directional calibration parameters to compensate, the action direction of the object can be obtained. However, the object 10 may need to be placed initially in a known direction and the precise placement at a known direction may be difficult to perform. The known direction in space with respect to the position tracking apparatus may be particularly difficult to determine precisely in the three-dimensional space.

Another approach is to use two points on the object to determine the directional calibration parameters. Although it may be easier to determine the calibration parameters for one point on an object, it may be more difficult to determine the calibration parameters for another point because of the object's geometry.

In the application of tracking a surgical needle, for example, the calibration parameters of a surgical needle's tip may be more easily determined because the tip itself can be regarded as a point. In contrast, however, the calibration parameters for a point on the needle's tail may be more difficult to measure because the tail is often not a geometric point. In cases where it is not convenient for the tracking marker to be mounted on the tip and there is a distance between the position of the tracking marker and the position of the needle tip, if the computed directional calibration parameters are not sufficiently accurate, significant positional errors may occur along the needle's elongated direction. As such, in many cases the tracking marker is mounted directly on the tip of a hollow surgical needle, so that the deviation is small between the needle and the tracking marker, allowing for a better operational accuracy.

A position tracking system according to some embodiments includes a position tracking apparatus and one or more tracking markers. The position tracking apparatus can track and provide position and direction information for the tracking markers in the three-dimensional space.

The coordinates used in the description below can be coordinates of the position tracking apparatus in the three-dimensional space.

The following description includes three sections: 1. Determining the directional calibration parameters for an object; 2. Determining the direction for an object; and 3. A tool used in determining the directional calibration parameters.

Figure 2:
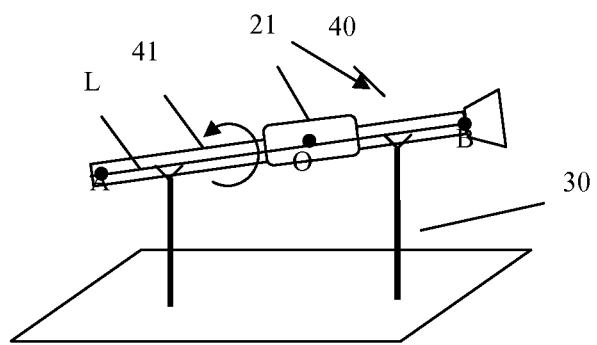
FIG. 2 is a positional diagram for points A, B on the object and point C on the tracking marker disposed over the object.
Figure 4:
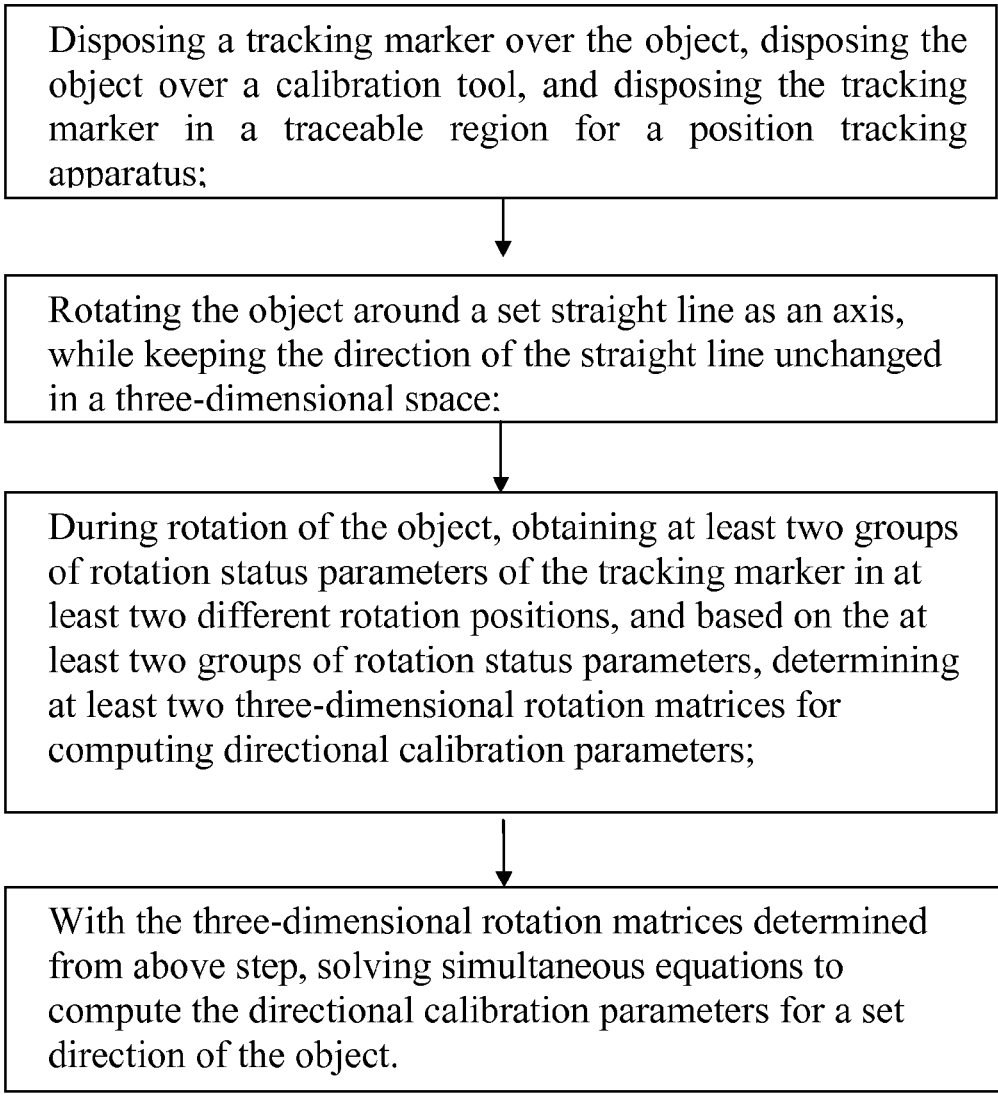
FIG. 4 is a flowchart of one embodiment to determine the directional calibration parameters for the object.

1. Determining the Directional Calibration Parameters for an Object;

FIG. 4 shows a flow chart of applying an embodiment of a method for determining the directional calibration parameters for the object. As shown in FIG. 2 and FIG. 4, the method for determining the directional calibration parameters for the object comprises:

a) disposing a tracking marker 21 over an object 40, then placing the object 40 on a calibration tool 30, and having the tracking marker 21 in the traceable region for a position tracking apparatus.

The object 40 may be directly replaced by the actual object that needs to be tracked. For example, the object 40 to be measured can be a dummy instrument for the purpose of measuring the directional calibration parameters, and the actual object to be tracked can be a surgical instrument.

b) with the aid of the calibration tool 30, rotating the object 40 around a set straight line L as an axis, while keeping the direction of the straight line L unchanged in the three-dimensional space.

The straight line L set for the object 40 may be located on the whole object 40, or on the part of the object, may also be located outside the object 40, as long as the object 40 is rotatable around the set straight line L as its rotation axis.

The disposing of the tracking marker 21 on the object 40 is fixed such that there is substantially no relative direction change between the tracking marker 21 and the line L in the three-dimensional space.

The tracking marker 21 mounted on the object 40 may be detachable. When re-attaching the tracking marker, it is ensured that substantially no relative direction change occurs between the tracking marker 21 and the line L in the three-dimensional space.

The restriction for relative direction change between the tracking marker 21 and the line L for the object in the three-dimensional space does not mean an absolute restriction for relative position change between the tracking marker 21 and the line L for the object in the three-dimensional space.

c) during rotation of the object 40, obtaining at least two groups of rotation status parameters of the tracking marker 21 in at least two different rotation positions via the position tracking apparatus. From the groups of rotation status parameters, determining at least two three-dimensional rotation matrices for computing directional calibration parameters.

The three-dimensional rotation matrix can be obtained according to the rotation status of the tracking marker using a position tracking apparatus.

In some implementations, the rotation status is expressed in the form of Euler angles: azimuth angle A (Azimuth), elevation angle E (Elevation), and roll angle R (Roll). The three-dimensional rotation matrix M $$\begin{bmatrix} M(1,1) & M(1,2) & M(1,3) \\ M(2,1) & M(2,2) & M(2,3) \\ M(3,1) & M(3,2) & M(3,3) \end{bmatrix}$$

has relationship with the angle A, the angle E and the angle R as follows:

$M(1,1)=\mathrm{COS}(E)\times\mathrm{COS}(A)$ $M(1,2)=\mathrm{COS}(E)\times\mathrm{SIN}(A)$ $M(1,3)=-\mathrm{SIN}(E)$ $M(2,1)=-(\mathrm{COS}(R)\times\mathrm{SIN}(A))+(\mathrm{SIN}(R)\times\mathrm{SIN}(E)\times\mathrm{COS}(A))$ $M(2,2)=(\mathrm{COS}(R)\times\mathrm{COS}(A))+(\mathrm{SIN}(R)\times\mathrm{SIN}(E)\times\mathrm{SIN}(A))$ $M(2,3)=\mathrm{SIN}(R)\times\mathrm{COS}(E)$ $M(3,1)=(\mathrm{SIN}(R)\times\mathrm{SIN}(A))+(\mathrm{COS}(R)\times\mathrm{SIN}(E)\times\mathrm{COS}(A))$ $M(3,2)=-(\mathrm{SIN}(R)\times\mathrm{COS}(A))+(\mathrm{COS}(R)\times\mathrm{SIN}(E)\times\mathrm{SIN}(A))$ $M(3,3)=\mathrm{COS}(R)\times\mathrm{COS}(E)$ As such, each element of the matrix M can be determined There may be different forms of rotation status and there are different relationships with the three-dimensional rotation matrix. In some implementations, the position tracking apparatus just outputs the three-dimensional rotation matrix in the right form as needed here.

d) with at least two three-dimensional rotation matrices determined from step c), solving simultaneous equations to compute the directional calibration parameters for the set direction of the object.

Figure 5:
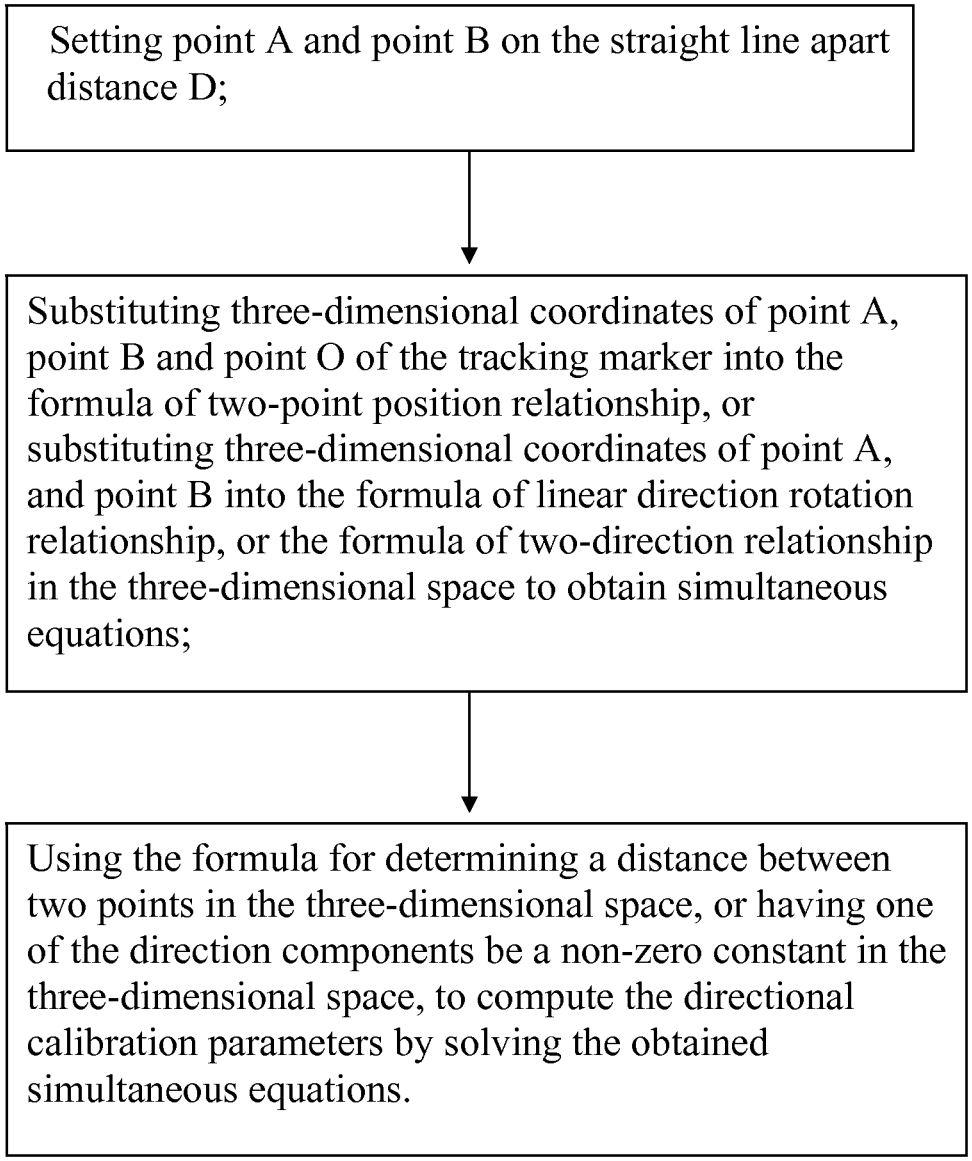
FIG. 5 is a flowchart of one embodiment to compute the directional calibration parameters.

FIG. 5 shows a flow chart of the embodiment to solve simultaneous equations to compute the directional calibration parameters.

The followings steps may be employed:

Setting point A and point B on the set straight line with a distance D apart (D is larger than 0); setting point O on the tracking marker's center to represent the tracking marker; setting three-dimensional coordinates A $(X_A, Y_A, Z_A)$ B$(X_B, Y_B, Z_B)$ and C$(X_C, Y_C, Z_C)$ respectively.

Substituting three-dimensional coordinates of point A, B, and O into the formula of the two-point position relationship in the three-dimensional space to obtain equations 1)-6):

$X_A = X_c + X_{AO} \times M_p(1,1) + Y_{AO} \times M_p(2,1) + Z_{AO} \times M_p(3,1)$  1);

$Y_A = Y_c + X_{AO} \times M_p(1,2) + Y_{AO} \times M_p(2,2) + Z_{AO} \times M_p(3,2)$  2);

$Z_A = Z_c + X_{AO} \times M_p(1,3) + Y_{AO} \times M_p(2,3) + Z_{AO} \times M_p(3,3)$  3);

$X_B = X_c + X_{BO} \times M_p(1,1) + Y_{BO} \times M_p(2,1) + Z_{BO} \times M_p(3,1)$  4);

$Y_B = Y_c + X_{BO} \times M_p(1,2) + Y_{BO} \times M_p(2,2) + Z_{BO} \times M_p(3,2)$  5);

$Z_B = Z_c + X_{BO} \times M_p(1,3) + Y_{BO} \times M_p(2,3) + Z_{BO} \times M_p(3,3)$  6);

where $X_{AO}, Y_{AO}, Z_{AO}$ are offset distances between point A and Point O, $X_{BO}, Y_{BO}, Z_{BO}$ are offset distances between point B and Point O.

When the tracking marker 21 is at "zero" direction, its rotation matrix becomes unit matrix, the displacement components between Point A and Point O are just $X_{AO}, Y_{AO}, Z_{AO}$, the displacement components between Point B and Point O are just $X_{BO}, Y_{BO}, Z_{BO}$.

The matrix $M_P$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing directional calibration parameters determined from step C), p=1, 2, ..., n, n is a positive integer greater than 1.

Setting $\delta x = X_A - X_B$, $\delta y = Y_A - Y_B$, $\delta z = Z_A - Z_B$, where $\delta x$, $\delta y$, $\delta z$ represent X, Y, Z components of the linear direction in three-dimensional coordinate system.

Equation 1)-Equation 4) results in Equation 7); Equation 2)-Equation 5) results in Equation 8): Equation 3)-Equation 6) results in Equation 9):

$$\delta x = X_{off} \times M_p(1,1) + Y_{off} \times M_p(2,1) + Z_{off} \times M_p(3,1) \quad\quad 7);$$

$$\delta y = X_{off} \times M_p(1,2) + Y_{off} \times M_p(2,2) + Z_{off} \times M_p(3,2) \quad\quad 8);$$

$$\delta z = X_{off} \times M_p(1,3) + Y_{off} \times M_p(2,3) + Z_{off} \times M_p(3,3) \quad\quad 9);$$

wherein $X_{off} = X_{AO} - X_{BO}$, $Y_{off} = Y_{AO} - Y_{BO}$, $Z_{off} = Z_{AO} - Z_{BO}$. $X_{off}, Y_{off}, Z_{off}$ are X, Y, Z components of directional calibration parameters for the set straight line for the tracked object. The equations 7)-9) are relationship equations for a linear direction rotation, or two-direction relationship equations.

When the tracking marker 21 is at "zero" direction, its rotation matrix will be unit matrix, X, Y, and Z components of direction of line L can be expressed as $X_{off} = \delta x^{(0)}$, $Y_{off} = \delta y^{(0)}$, $Z_{off} = \delta z^{(0)}$. It means that the directional calibration parameters of $X_{off}, Y_{off}, Z_{off}$ are just direction components of line L when line L is at "zero" direction. Then it is easily understood that the equations 7)-9) describe the principle for line L to turn its "zero" direction to another direction, or linear direction $\delta x$, $\delta y$, $\delta z$ (X, Y, Z components) will be its "zero" direction $X_{off}, Y_{off}, Z_{off}$ (X, Y, Z components) multiplied by the rotation matrix. The equations 7)-9) are regarded as the formula of the two-direction relationship.

To compute the directional calibration parameters $X_{off}, Y_{off}, Z_{off}$, an implementation is to use the formula for determining the distance between the two points, which is the following:

The formula of distance D between point A and point B is $$D = \sqrt{(X_A - X_B)^2 + (Y_A - Y_B)^2 + (Z_A - Z_B)^2},$$

or $$D = \sqrt{\delta x^2 + \delta y^2 + \delta z^2} \quad\quad 10);$$

wherein D is known number greater than 0. Substituting each three-dimensional rotation matrix for computing directional calibration parameters determined from step C) into equations 7)-9), plus equation 10), constitutes simultaneous equations. Solving the combined simultaneous equations gives $X_{off}, Y_{off}, Z_{off}$.

Suppose that $M_1$ and $M_2$ are two determined three-dimensional rotation matrices for determining directional calibration and are expressed as:

$$\begin{bmatrix} M_1(1,1) & M_1(1,2) & M_1(1,3) \\ M_1(2,1) & M_1(2,2) & M_1(2,3) \\ M_1(3,1) & M_1(3,2) & M_1(3,3) \end{bmatrix}$$

and $$\begin{bmatrix} M_2(1,1) & M_2(1,2) & M_2(1,3) \\ M_2(2,1) & M_2(2,2) & M_2(2,3) \\ M_2(3,1) & M_2(3,2) & M_2(3,3) \end{bmatrix}$$

Then from equations 7)-9), below equations 11)-16) are obtained:

$$\delta x = X_{off} \times M_1(1,1) + Y_{off} \times M_1(2,1) + Z_{off} \times M_1(3,1) \quad\quad 11);$$

$$\delta y = X_{off} \times M_1(1,2) + Y_{off} \times M_1(2,2) + Z_{off} \times M_1(3,2) \quad\quad 12);$$

$$\delta z = X_{off} \times M_1(1,3) + Y_{off} \times M_1(2,3) + Z_{off} \times M_1(3,3) \quad\quad 13);$$

$$\delta x = X_{off} \times M_2(1,1) + Y_{off} \times M_2(2,1) + Z_{off} \times M_2(3,1) \quad\quad 14);$$

$$\delta y = X_{off} \times M_2(1,2) + Y_{off} \times M_2(2,2) + Z_{off} \times M_2(3,2) \quad\quad 15);$$

$$\delta z = X_{off} \times M_2(1,3) + Y_{off} \times M_2(2,3) + Z_{off} \times M_2(3,3) \quad\quad 16);$$

Solving the above simultaneous equations 10)-16) with equation 10) combined will give $X_{off}, Y_{off}, Z_{off}$.

If using more than two three-dimensional rotation matrix, like $M_3, M_4 \ldots$ to solve $X_{off}, Y_{off}, Z_{off}$ the number of equations will be more than the number of unknowns. Solving further equations by other methods (e.g. some iterative method) will obtain a more accurate solution for $X_{off}, Y_{off}, Z_{off}$.

To compute the directional calibration parameters $X_{off}, Y_{off}, Z_{off}$, another implementation is to have one of the components of the direction be a non-zero constant, which is the following:

At least one of the linear directions X, Y, Z components is not zero (in other words, the line is not perpendicular to at least one of X, Y, Z axes).

Among $\delta x$, $\delta y$, $\delta z$, set a non-zero component as known non-zero constant. Substitute each three-dimensional rotation matrix for computing directional calibration parameters determined from step c) into equations 7)-9), to obtain non-homogeneous linear equations. Solving the non-homogeneous linear equations gives $X_{off}, Y_{off}, Z_{off}$.

For example, the object is seated in a direction that is not perpendicular to X axis, then $\delta x$ is not zero, $\delta x$=constant. When $M_1$ and $M_2$ are two determined three-dimensional rotation matrix for determining directional calibration, then from equations 7)-9), equations 17)-22) can be obtained:

$$\text{const} = X_{off} \times M_1(1,1) + Y_{off} \times M_1(2,1) + Z_{off} \times M_1(3,1) + 0 + 0 \quad\quad 17);$$

$$0 = X_{off} \times M_1(1,2) + Y_{off} \times M_1(2,2) + Z_{off} \times M_1(3,2) - \delta y + 0 \quad\quad 18);$$

$$0 = X_{off} \times M_1(1,3) + Y_{off} \times M_1(2,3) + Z_{off} \times M_1(3,3) + 0 - \delta z \quad\quad 19);$$

$$\text{const} = X_{off} \times M_2(1,1) + Y_{off} \times M_2(2,1) + Z_{off} \times M_2(3,1) + 0 + 0 \quad\quad 20);$$

$$0 = X_{off} \times M_2(1,2) + Y_{off} \times M_2(2,2) + Z_{off} \times M_2(3,2) - \delta y + 0 \quad\quad 21);$$

$$0 = X_{off} \times M_2(1,3) + Y_{off} \times M_2(2,3) + Z_{off} \times M_2(3,3) + 0 - \delta z \quad\quad 22);$$

Equations of 17)-22) compose a set of non-homogeneous linear equations regarding unknown numbers of $X_{off}, Y_{off}, Z_{off}, \delta x, \delta y, \delta z$. Solving the equation set will give $X_{off}, Y_{off}, Z_{off}$.

If using more than two three-dimensional rotation matrices, such as $M_3, M_4 \ldots$, to solve $X_{off}, Y_{off}, Z_{off}$ the number of equations may be more than the number of unknowns. Solving further equations by other methods (e.g., using an iterative method) will obtain a more accurate solution for $X_{off}$, $Y_{off}$, $Z_{off}$.

It may be noted that $X_{off}$, $Y_{off}$, $Z_{off}$ can be determined by the relative direction in the three-dimensional space between the set line L and tracking marker 21. It is not dependent on the positions of the two points A, B on the line L. As long as the object's rotation remains around the unchanged linear direction as the axis during the process of obtaining different rotation status parameters, the solved $X_{off}$, $Y_{off}$, $Z_{off}$ can be unique for that relative direction between the set line L and the tracking marker 21 mounted on the object. Otherwise, if the relative direction is changed between the line L and the tracking marker 21 for the object, the solved $X_{off}$, $Y_{off}$, $Z_{off}$ will be different.

In some embodiments, the method of determining the directional calibration parameters for the object comprises: keeping the linear direction unchanged for the object, obtaining plurality of rotating status parameters to deduce the directional calibration parameters with the formula of two-point position relationship or linear direction rotation relationship in the three-dimensional space.

2. Determining the Direction for Tracked Objects;

Determining the directional calibration parameters for the object may be performed and completed before actually tracking the target objects. The determined directional calibration parameters can be used in determining the action direction of the object during the tracking process.

FIG. 6 shows a flow chart of one embodiment of the method for determining the action direction for the object. As shown in FIG. 6, the method may comprise:

a) disposing a tracking marker over an object, in a way that the relative direction or angle in the three-dimensional space between the direction of the straight line for the object and the tracking marker is substantially the same as the relative direction or angel in the three-dimensional space between the direction of the straight line for the object and the tracking marker during the determination of the directional calibration parameters.

The object used during the process of determining the directional calibration parameters may be different from the object to be tracked.

Putting the tracking marker in the traceable region for the position tracking apparatus.

The mounting of the tracking marker on the object is fixed so that there is no relative direction change between the tracking marker and the object in the three-dimensional space.

The tracking marker fixed on the object may be detachable. When re-attaching the tracking marker, it is ensured that no relative direction change between the tracking marker and the object in the three-dimensional space.

The restriction for relative direction change between the tracking marker and the object in the three-dimensional space does not mean an absolute restriction for relative position change between the tracking marker and the object in the three-dimensional space.

b) during tracking, obtaining the rotation status parameters in three-dimensional space of the tracking marker via the position tracking apparatus, to determine the three-dimensional rotation matrix $M_S$.

The three-dimensional rotation matrix can be obtained according to the rotation status of the tracking marker by the position tracking apparatus.

In some implementations, the position track apparatus just outputs the three-dimensional rotation matrix in the right form as needed here.

c) with the three-dimensional rotation matrix determined from step b), compute the action direction for the object.

The action direction means the direction that needs to be tracked in the use of the object.

The action direction may be a linear direction on the whole object, or on the part of the object, or may be located outside.

Figure 7:
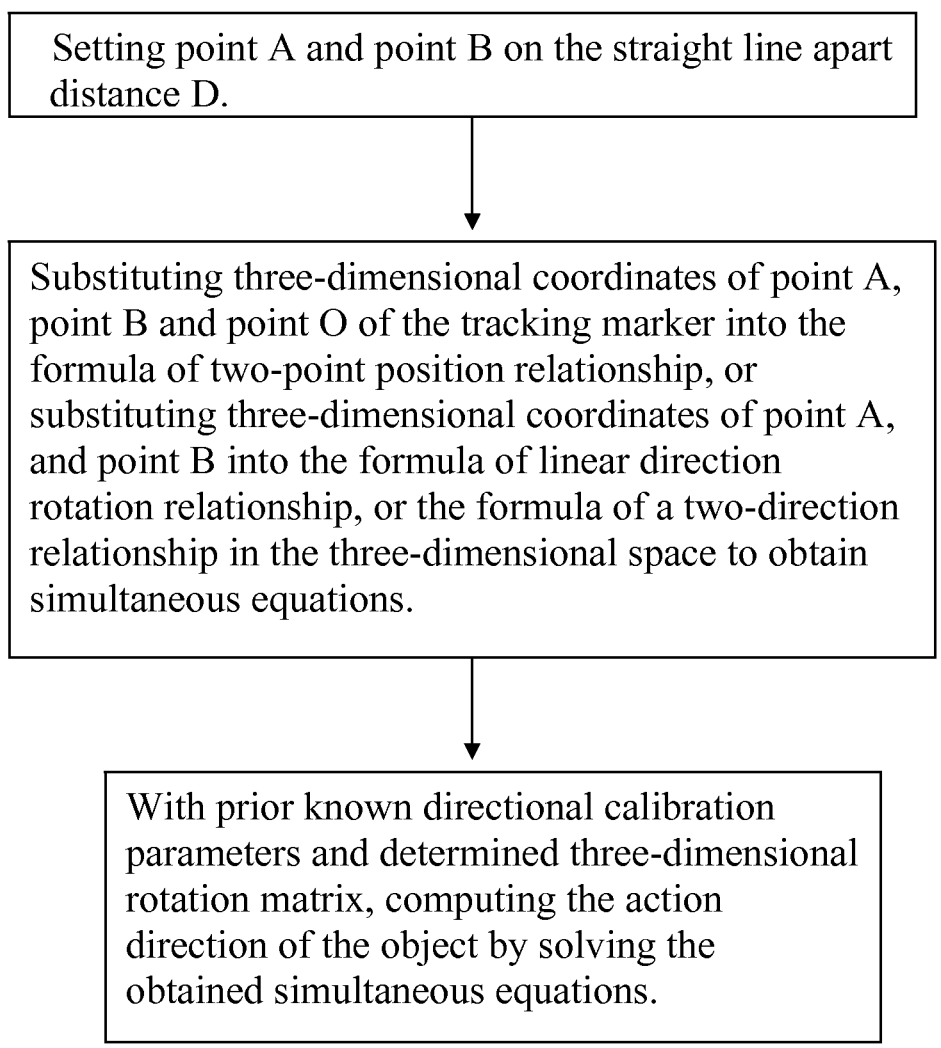
FIG. 7 is a flowchart of one embodiment to compute the action direction.

FIG. 7 shows a flow chart of one embodiment to compute the tracked direction.

The process may include:

Setting point A and point B on the set straight line; setting point O on the tracking marker's center to represent the tracking marker; setting three-dimensional coordinates A ($X_{A\_S}$, $Y_{A\_S}$, $Z_{A\_S}$), B($X_{B\_S}$, $Y_{B\_S}$, $Z_{B\_S}$) and C ($X_{c\_S}$, $Y_{c\_S}$, $Z_{c\_S}$) respectively.

Substituting three-dimensional coordinates of point A, B and O into the formula of the two-point position relationship in the three-dimensional space to obtain equations 23)-28):

$$X_{A\_S} = X_{c\_S} + X_{AO} \times M_S(1,1) + Y_{AO} \times M_S(2,1) + Z_{AO} \times M_S(3,1) \quad \quad (23);$$

$$Y_{A\_S} = Y_{c\_S} + X_{AO} \times M_S(1,2) + Y_{AO} \times M_S(2,2) + Z_{AO} \times M_S(3,2) \quad \quad (24);$$

$$Z_{A\_S} = Z_{c\_S} + X_{AO} \times M_S(1,3) + Y_{AO} \times M_S(2,3) + Z_{AO} \times M_S(3,3) \quad \quad (25);$$

$$X_{B\_S} = X_{c\_S} + X_{BO} \times M_S(1,1) + Y_{BO} \times M_S(2,1) + Z_{BO} \times M_S(3,1) \quad \quad (26);$$

$$Y_{B\_S} = Y_{c\_S} + X_{BO} \times M_S(1,2) + Y_{BO} \times M_S(2,2) + Z_{BO} \times M_S(3,2) \quad \quad (27);$$

$$Z_{B\_S} = Z_{c\_S} + X_{BO} \times M_S(1,3) + Y_{BO} \times M_S(2,3) + Z_{BO} \times M_S(3,3) \quad \quad (28);$$

wherein $X_{AO}$, $Y_{AO}$, $Z_{AO}$ are offset distances between point A and Point O, and $X_{BO}$, $Y_{BO}$, $Z_{BO}$ are offset distances between point B and Point O.

When the tracking marker is at "zero" direction, its rotation matrix becomes unit matrix, the displacement components between Point A and Point O are just $X_{AO}$, $Y_{AO}$, $Z_{AO}$, and the displacement components between Point B and Point O are just $X_{BO}$, $Y_{BO}$, $Z_{BO}$. The matrix $M_S$ $$\begin{bmatrix} M_S(1,1) & M_S(1,2) & M_S(1,3) \\ M_S(2,1) & M_S(2,2) & M_S(2,3) \\ M_S(3,1) & M_S(3,2) & M_S(3,3) \end{bmatrix}$$

is the current three-dimensional rotation matrix for computing action direction determined from step b).

Setting $\delta x\_s = X_{A\_S} - X_{B\_S}$, $\delta y\_s = Y_{A\_S} - Y_{B\_S}$, $\delta z\_s = Z_{A\_S} - Z_{B\_S}$, where $\delta x\_s$, $\delta y\_s$, $\delta z\_s$ represent X, Y, Z components of the linear direction in three-dimensional coordinate system.

Equation 23)-Equation 26) results in Equation 29); Equation 24-Equation 27) results in Equation 30): Equation 25)-Equation 28) results in Equation 31):

$$\delta x\_s = X_{off} \times M_S(1,1) + Y_{off} \times M_S(2,1) + Z_{off} \times M_S(3,1) \quad \quad (29);$$

$$\delta y\_s = X_{off} \times M_S(1,2) + Y_{off} \times M_S(2,2) + Z_{off} \times M_S(3,2) \quad \quad (30);$$

$$\delta z\_s = X_{off} \times M_S(1,3) + Y_{off} \times M_S(2,3) + Z_{off} \times M_S(3,3) \quad \quad (31);$$

wherein $X_{off} = X_{AO} - X_{BO}$, $Y_{off} = Y_{AO} - Y_{BO}$, $Z_{off} = Z_{AO} - Z_{BO}$. $X_{off}$, $Y_{off}$, $Z_{off}$ are X, Y, Z components of directional calibration parameters for the set straight line for the object. The equations 29)-31) are relationship equations for a linear direction, or for a two-direction rotation.

The equations 29)-31) describe the principle that a linear direction $\delta x\_s, \delta y\_s, \delta z\_s$ (X, Y, Z components) will be its "zero" direction $X_{off}, Y_{off}, Z_{off}$(X, Y, Z components) multiplied by the rotation matrix.

With prior known directional calibration parameters $X_{off}, Y_{off}, Z_{off}$ and determined three-dimensional rotation matrix $M_S$, equations 29)-31) just give $\delta x\_s, \delta y\_s, \delta z\_s$ of the action direction.

In some embodiments, the method for determining the direction for the object is: obtaining current rotating status parameters, using prior known directional calibration parameters to deduce the direction with the principles of two-point position relationship or linear direction rotation relationship in the three-dimensional space.

The method does not require determining a set of two points on the linear direction for the object.

3. A Calibration Tool Used for Determining the Directional Calibration Parameters.

Figure 3:
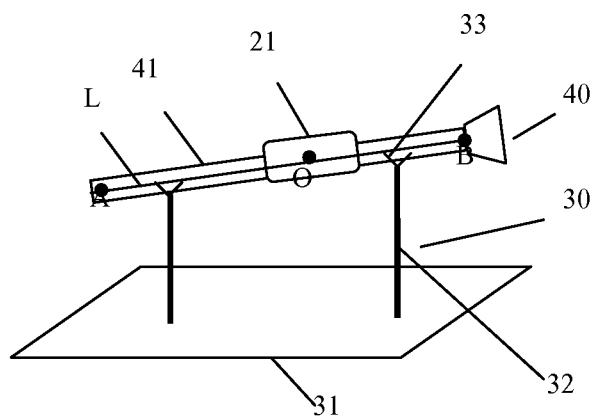
FIG. 3 is a block diagram showing an embodiment of the calibration tool.

The present disclosure discloses a tool for determining the directional calibration parameters. As shown in FIG. 3, the calibration tool includes a chassis 31. A holding bracket 32 is set on the chassis 31 for holding the object 40, which may have a tracking marker 21 disposed thereon. The holding bracket 32 ensures the direction of the set straight line L for the object 40 remain unchanged in the three-dimensional space, while the cylindrical part 41 of the object 40 rotates around the set straight line L.

As shown in FIG. 3, the bracket 32 may be provided in pairs. Each bracket 32 is provided with holding portion 33, which may be V-shaped, ring-shaped, arc-shaped, or other shapes. At least two points at holding portion 33 will support the cylindrical part 41 of the object 40, so that the object 40 may be stabilized at a fixed spatial direction, and can rotate around the set line L as it axis, while keeping the direction of L unchanged.

The size of the open degree of V-shape, or bend degree of arc/ring for the portion 33 can be adjusted. The distance between brackets 32 is adjustable. This tool plays a role to support, clamp and fix the object. The tool can assist the object to rotate around the set line as an axis while keeping the direction of line unchanged. The tool can ensure fast and accurate measurement of the directional calibration parameters.

Compared with existing methods which need to place the object in a known direction, the present disclosure's method of determining the directional calibration parameters does not have such a requirement. By applying the position tracking apparatus, the directional calibration parameters can be computed via the rotation status parameters of the tracking marker mounted on the object. The operation is easy.

Furthermore, a method of determining the directional calibration parameters does not require computing the calibration parameters for two-point set on the straight line representing the direction of the object, and has nothing to do with the positions of the two points.

The embodiments disclosed herein may be applicable to any case that needs to determine the linear direction of an object with position tracking apparatus.

In medical applications, the action direction information for some surgical instruments may be important for doctors to achieve a precise procedure. The present disclosure is applicable to any surgical instrument that needs to determine a linear direction on a whole or a part of the instrument, such as surgical needles, surgical drills, and implant screws. Another example is a surgical clamp with a flexible endoscope. Although a flexible hose of this type of apparatus does not necessarily have a linear direction, the less flexible portion such as the clamp portion at the head of the apparatus can still have an action direction, which can be determined by the method disclosed herein. Furthermore, the method is also applicable to cases where the linear direction may be defined by a beam from a surgical instrument. For example, radiation, lasers, or particles emitted from the surgical instrument may have linear directions, which can also be determined by the methods disclosed herein.

Although specific embodiments have been described above in detail, the description is merely for purposes of illustration. It should be appreciated, therefore, that many aspects described above are not intended as required or essential elements unless explicitly stated otherwise. Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A method of determining directional calibration parameters of an object to be tracked, the method comprising:
   a) disposing a tracking marker over the object, disposing the object over a calibration tool, and disposing the tracking marker in a traceable region for a position tracking apparatus, wherein the position tracking apparatus is configured to receive signal from, and deduce at least direction of, the tracking marker in the three-dimensional space;
   b) rotating the object around a set straight line as an axis, while keeping the direction of the straight line unchanged in a three-dimensional space;
   c) during rotation of the object, obtaining at least two groups of rotation status parameters of the tracking marker in at least two different rotation positions, and based on the at least two groups of rotation status parameters, determining at least two three-dimensional rotation matrices for computing the directional calibration parameters;
   d) with the three-dimensional rotation matrices determined from step c), solving simultaneous equations to compute the directional calibration parameters for a set direction of the object.

2. The method of claim 1, wherein the calibration tool comprises a chassis and a holding bracket, and wherein the holding bracket is set on the chassis for holding the object mounted with the tracking marker such that the holding bracket makes the direction of the straight line for the object remain unchanged in the three-dimensional space, while still allowing the object to rotate around the axis.

3. The method according to claim 1, wherein the position tracking apparatus is at least one of infrared tracking apparatus or electromagnetic tracking apparatus.

4. The method of claim 1, wherein the simultaneous equations in step d) are derived from at least one of a formula of two-point position relationship, a formula of two-direction relationship, or a formula of linear direction rotation relationship in the three-dimensional space.

5. The method of claim 4, wherein the derivation of the simultaneous equations from the formula of two-point position relationship comprises:
   setting point A and point B on the set straight line with a distance D apart, wherein D is a number larger than 0;
   setting point O on the tracking marker's center to represent the tracking marker; setting three-dimensional coordinates A ($X_A$, $Y_A$, $Z_A$), B($X_B$, $Y_B$, $Z_B$) and C(Xc, Zc) respectively;

substituting the three-dimensional coordinates of point A, B, and O into the formula of a two-point position relationship in the three-dimensional space to obtain simultaneous equations 1)-9):

$$X_A = X_c + X_{AO} \times M_p(1,1) + Y_{AO} \times M_p(2,1) + Z_{AO} \times M_p(3,1) \quad 1);$$

$$Y_A = Y_c + X_{AO} \times M_p(1,2) + Y_{AO} \times M_p(2,2) + Z_{AO} \times M_p(3,2) \quad 2);$$

$$Z_A = Z_c + X_{AO} M_p(1,3) + Y_{AO} \times M_p(2,3) + Z_{AO} \times M_p(3,3) \quad 3);$$

$$X_B = X_c + X_{BO} \times M_p(1,1) + Y_{BO} \times M_p(2,1) + Z_{BO} \times M_p(3,1) \quad 4);$$

$$Y_B = Y_c + X_{BO} \times M_p(1,2) + Y_{BO} \times M_p(2,2) + Z_{BO} \times M_p(3,2) \quad 5);$$

$$Z_B = Z_c + X_{BO} \times M_p(1,3) + Y_{BO} \times M_p(2,3) + Z_{BO} \times M_p(3,3) \quad 6);$$

$$X_{off} = X_{AO} - X_{BO} \quad 7);$$

$$Y_{off} = Y_{AO} - Y_{BO} \quad 8);$$

$$Z_{off} = Z_{AO} - Z_{BO} \quad 9);$$

wherein $X_{AO}$, $Y_{AO}$, $Z_{AO}$ are offset distances between point A and point O; $X_{BO}$, $Y_{BO}$, $Z_{BO}$ are offset distances between point B and point O; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, ..., n, where n is a positive integer greater than 1; $X_{off}$, $Y_{off}$, $Z_{off}$ are X, Y, Z components of the directional calibration parameters for the set straight line for the object.

6. The method of claim 4, wherein the derivation of the simultaneous equations from the formula of linear direction rotation relationship, or from the formula of two-direction relationship comprises:

setting $\delta x = X_A - X_B$, $\delta y = Y_A - Y_B$, $\delta z = Z_A - Z_B$, where $\delta x$, $\delta y$, $\delta z$ represent X, Y, Z components of the linear direction in three-dimensional coordinate system;

obtaining equations 10)-12) based on the formula of a linear direction rotation relationship, or the formula of a two-direction relationship:

$$\delta x = X_{off} \times M_p(1,1) + Y_{off} \times M_p(2,1) + Z_{off} \times M_p(3,1) \quad 10);$$

$$\delta y = X_{off} \times M_p(1,2) + Y_{off} \times M_p(2,2) + Z_{off} \times M_p(3,2) \quad 11);$$

$$\delta z = X_{off} \times M_p(1,3) + Y_{off} \times M_p(2,3) + Z_{off} \times M_p(3,3) \quad 12);$$

wherein $X_{off}$, $Y_{off}$, $Z_{off}$ are X, Y, Z components of the directional calibration parameters for the set straight line for the object, or are X, Y, Z components of "zero" direction; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, ..., n, where n is a positive integer greater than 1.

7. The method of claim 4, wherein the simultaneous equations in step d) are solved based on at least one formula for determining a distance between two points in the three-dimensional space.

8. The method of claim 7, wherein said solving the simultaneous equations comprises:

setting point A and point B on the set straight line with a distance D apart, wherein D is a number larger than 0; setting point O on the tracking marker's center to represent the tracking marker; setting three-dimensional coordinates A $(X)_A$, $Y_A$, $Z_A$), B ($X_B$, $Y_B$, $Z_B$) and C(Xc, Yc, Zc) respectively;

substituting the three-dimensional coordinates of point A, B, and O into the formula of a two-point position relationship in the three-dimensional space to obtain simultaneous equations 1)-9):

$$X_A = X_c + X_{AO} \times M_p(1,1) + Y_{AO} \times M_p(2,1) + Z_{AO} \times M_p(3,1) \quad 1);$$

$$Y_A = Y_c + X_{AO} \times M_p(1,2) + Y_{AO} \times M_p(2,2) + Z_{AO} \times M_p(3,2) \quad 2);$$

$$Z_A = Z_c + X_{AO} \times M_p(1,3) + Y_{AO} \times M_p(2,3) + Z_{AO} \times M_p(3,3) \quad 3);$$

$$X_B = X_c + X_{BO} \times M_p(1,1) + Y_{BO} \times M_p(2,1) + Z_{BO} \times M_p(3,1) \quad 4);$$

$$Y_B = Y_c + X_{BO} \times M_p(1,2) + Y_{BO} \times M_p(2,2) + Z_{BO} \times M_p(3,2) \quad 5);$$

$$Z_B = Z_c + X_{BO} \times M_p(1,3) + Y_{BO} \times M_p(2,3) + Z_{BO} \times M_p(3,3) \quad 6);$$

$$X_{off} = X_{AO} - X_{BO} \quad 7);$$

$$Y_{off} = Y_{AO} - Y_{B0} \quad 8);$$

$$Z_{off} = Z_{AO} - Z_{BO} \quad 9);$$

wherein $X_{AO}$, $Y_{AO}$, $Z_{AO}$ are offset distances between point A and point O; $X_{BO}$, $Y_{BO}$, $Z_{BO}$ are offset distances between point B and point O; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, ..., n, where n is a positive integer greater than 1; $X_{off}$, $Y_{off}$, $Z_{off}$ are X Y, Z components of the directional calibration parameters for the set straight line for the object;

setting $\delta x = X_A - X_B$, $\delta y = Y_A - Y_B$, $\delta z = Z_A - Z_B$, where $\delta x$, $\delta y$, $\delta z$ represent X, Y, Z components of the linear direction in three-dimensional coordinate system;

obtaining equations 10)-12) based on the formula of a linear direction rotation relationship, or the formula of a two-direction relationship:

$$\delta x = X_{off} \times M_p(1,1) + Y_{off} \times M_p(2,1) + Z_{off} \times M_p(3,1) \quad 10);$$

$$\delta y = X_{off} \times M_p(1,2) + Y_{off} \times M_p(2,2) + Z_{off} \times M_p(3,2) \quad 11);$$

$$\delta z = X_{off} \times M_p(1,3) + Y_{off} \times M_p(2,3) + Z_{off} \times M_p(3,3) \quad 12);$$

wherein $X_{off}$, $Y_{off}$, $Z_{off}$ are X, Y, Z components of the directional calibration parameters for the set straight line for the object, or are X, Y, Z components of "zero" direction; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, ..., n, where n is a positive integer greater than 1;

setting the equation to determine the distance between the two points in the three-dimensional space:

$$D=\sqrt{(X_A-X_B)^2+(Y_A-Y_B)^2+(Z_A-Z_B)^2};$$

or $$D=\sqrt{\delta x^2+\delta y^2+\delta z^2} \qquad 13);$$

wherein D is greater than 0;
substituting each three-dimensional rotation matrix for computing the directional calibration parameters into equations 1)-9), plus equation 13), to obtain the simultaneous equations; or
substituting each three-dimensional rotation matrix for computing the directional calibration parameters into equations 10)-12), plus equation 13), to obtain the simultaneous equations.

9. The method of claim 4, wherein the simultaneous equations in step d) are solved by having one of the components of the direction be a non-zero constant in the three-dimensional space.

10. The method of claim 9, wherein said solving the simultaneous equations comprises:
setting point A and point B on the set straight line with a distance D apart, wherein D is a number larger than 0; setting point O on the tracking marker's center to represent the tracking marker; setting three-dimensional coordinates A $(X_A, Y_A, Z_A)$, B$(X_B, Y_B, Z_B)$ and C(Xc, Yc, Zc) respectively;
substituting the three-dimensional coordinates of point A, B, and O into the formula of a two-point position relationship in the three-dimensional space to obtain simultaneous equations 1)-9):

$$X_A = X_c + X_{AO} \times M_p(1,1) + Y_{AO} \times M_p(2,1) + Z_{AO} \times M_p(3,1) \qquad 1);$$

$$Y_A = Y_c + X_{AO} \times M_p(1,2) + Y_{AO} \times M_p(2,2) + Z_{AO} \times M_p(3,2) \qquad 2);$$

$$Z_A = Z_c + X_{AO} \times M_p(1,3) + Y_{AO} \times M_p(2,3) + Z_{AO} \times M_p(3,3) \qquad 3);$$

$$X_B = X_c + X_{BO} \times M_p(1,1) + Y_{BO} \times M_p(2,1) + Z_{BO} \times M_p(3,1) \qquad 4);$$

$$Y_B = Y_c + X_{BO} \times M_p(1,2) + Y_{BO} \times M_p(2,2) + Z_{BO} \times M_p(3,2) \qquad 5);$$

$$Z_B = Z_c + X_{BO} \times M_p(1,3) + Y_{BO} \times M_p(2,3) + Z_{BO} \times M_p(3,3) \qquad 6);$$

$$X_{off} = X_{AO} - X_{BO} \qquad 7);$$

$$Y_{off} = Y_{AO} - Y_{BO} \qquad 8);$$

$$Z_{off} = Z_{AO} - Z_{BO} \qquad 9);$$

wherein $X_{AO}, Y_{AO}, Z_{AO}$ are offset distances between point A and point O; $X_{BO}, Y_{BO}, Z_{BO}$ are offset distances between point B and point O; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, ..., n, where n is a positive integer greater than 1; $X_{off}, Y_{off}, Z_{off}$ are X, Y, Z components of the directional calibration parameters for the set straight line for the object;

setting $\delta x = X_A - X_B$, $\delta y = Y_A - Y_B$, $\delta z = Z_A - Z_B$, where $\delta x$, $\delta y$, $\delta z$ represent X, Y, Z components of the linear direction in three-dimensional coordinate system;

obtaining equations 10)-12) based on the formula of a linear direction rotation relationship, or the formula of a two-direction relationship:

$$\delta x = X_{off} \times M_p(1,1) + Y_{off} \times M_p(2,1) + Z_{off} \times M_p(3,1) \qquad 10);$$

$$\delta y = X_{off} \times M_p(1,2) + Y_{off} \times M_p(2,2) + Z_{off} \times M_p(3,2) \qquad 11);$$

$$\delta z = X_{off} \times M_p(1,3) + Y_{off} \times M_p(2,3) + Z_{off} \times M_p(3,3) \qquad 12);$$

wherein $X_{off}, Y_{off}, Z_{off}$ are X, Y, Z components of the directional calibration parameters for the set straight line for the object, or are X, Y, Z components of "zero" direction; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, ..., n, where n is a positive integer greater than 1;

among $\delta x$, $\delta y$, $\delta z$, setting a non-zero component as known non-zero constant; substituting each three-dimensional rotation matrix for computing the directional calibration parameters into equations 10)-12), to obtain non-homogeneous linear equations; or among $X_A - X_B$, $Y_A - Y_B$, $Z_A - Z_B$, setting a non-zero component as known non-zero constant; substituting each three-dimensional rotation matrix for computing the directional calibration parameters into equations 1)-9), to obtain non-homogeneous linear equations.

11. A method of determining an action direction of an object to be tracked, the method comprising:
a) mounting a tracking marker on the object, such that a relative direction or angle in a three-dimensional space between a direction of a straight line for the object and the tracking marker is same as the relative direction or angel in the three-dimensional space between the direction of the straight line for the object and the tracking marker during determination of directional calibration parameters, and disposing the tracking marker in a traceable region for a position tracking apparatus, wherein the position tracking apparatus is configured to receive signal from, and deduce at least direction of, the tracking marker in the three-dimensional space;
b) during tracking, obtaining the rotation status parameters of the tracking marker in the three-dimensional space via the position tracking apparatus to determine the three-dimensional rotation matrix;
c) based on the three-dimensional rotation matrix determined from step b), solving simultaneous equations to compute the action direction of the object.

12. The method of claim 11, wherein the mounting of the tracking marker on the object is detachable.

13. The method according to claim 11, wherein the position tracking apparatus is at least one of infrared tracking apparatus or electromagnetic tracking apparatus.

14. The method of claim 11, wherein the simultaneous equations are derived from at least one of a formula of a two-point position relationship, a formula of a two-direction relationship, or a formula of a linear direction rotation relationship in the three-dimensional space.

15. The method of claim 14, wherein the derivation of the simultaneous equations from the formula of two-point position relationship includes:

setting point A and point B on the set straight line; setting point O on the tracking marker's center to represent the tracking marker; setting three-dimensional coordinates A $(X_{A\_S}, Y_{A\_S}, Z_{A\_S})$, B$(X_{B\_S}, Y_{B\_S}, Z_{B\_S})$ and C $(X_{c\_S}, Y_{c\_S}, Z_{c\_S})$ respectively;

substituting three-dimensional coordinates of point A, B and O into the formula of the two-point position relationship in the three-dimensional space to obtain equations 14)-19):

$$X_{A\_S}=X_{c\_S}+X_{AO}\times M_S(1,1)+Y_{AO}\times M_S(2,1)+Z_{AO}\times M_S(3,1) \quad 14);$$

$$Y_{A\_S}=Y_{c\_S}+X_{AO}\times M_S(1,2)+Y_{AO}\times M_S(2,2)+Z_{AO}\times M_S(3,2) \quad 15);$$

$$Z_{A\_S}=Z_{c\_S}+X_{AO}\times M_S(1,3)+Y_{AO}\times M_S(2,3)+Z_{AO}\times M_S(3,3) \quad 16);$$

$$X_{B\_S}=X_{c\_S}+X_{BO}\times M_S(1,1)+Y_{BO}\times M_S(2,1)+Z_{BO}\times M_S(3,1) \quad 17);$$

$$Y_{B\_S}=Y_{c\_S}+X_{BO}\times M_S(1,2)+Y_{BO}\times M_S(2,2)+Z_{BO}\times M_S(3,2) \quad 18);$$

$$Z_{B\_S}=Z_{c\_S}+X_{BO}\times M_S(1,3)+Y_{BO}\times M_S(2,3)+Z_{BO}\times M_S(3,3) \quad 19);$$

wherein $X_{AO}, Y_{AO}, Z_{AO}$ are offset distances between point A and point O, and $X_{BO}, Y_{BO}, Z_{BO}$ are offset distances between point B and point O; $X_{off}=X_{AO}-X_{BO}$, $Y_{off}=Y_{AO}-Y_{BO}$, $Z_{off}=Z_{AO}-Z_{BO}$; $X_{off}, Y_{off}, Z_{off}$ are prior known X, Y, Z components of the directional calibration parameters for the set straight line for the object; $X_{A\_S}-X_{B\_S}, Y_{A\_S}-Y_{B\_S}, Z_{A\_S}-Z_{B\_S}$, representing X, Y, Z components of the linear direction in three-dimensional coordinate system;

the matrix $M_S$ $$\begin{bmatrix} M_S(1,1) & M_S(1,2) & M_S(1,3) \\ M_S(2,1) & M_S(2,2) & M_S(2,3) \\ M_S(3,1) & M_S(3,2) & M_S(3,3) \end{bmatrix}$$

is the current three-dimensional rotation matrix for computing action direction.

16. The method of claim 14, wherein the derivation of the simultaneous equations from the formula of the linear direction rotation relationship, or from the formula of the two-direction relationship comprises:

setting $\delta x\_s=X_{A\_S}-X_{B\_S}$, $\delta y\_s=Y_{A\_S}-Y_{B\_S}$, $\delta z\_s=Z_{A\_S}-Z_{B\_S}$, wherein $\delta x\_s, \delta y\_s, \delta z\_s$ represent X, Y, Z components of the linear direction in three-dimensional coordinate system;

obtaining equations 20)-22) based on the formula of linear direction rotation relationship, or the formula of a two-direction relationship, equation 20)-22) are:

$$\delta x\_s=X_{off}\times M_S(1,1)+Y_{off}\times M_S(2,1)+Z_{off}\times M_S(3,1) \quad 20);$$

$$\delta y\_s=X_{off}\times M_S(1,2)+Y_{off}\times M_S(2,2)+Z_{off}\times M_S(3,2) \quad 21);$$

$$\delta z\_s=X_{off}\times M_S(1,3)+Y_{off}\times M_S(2,3)+Z_{off}\times M_S(3,3) \quad 22);$$

wherein $X_{off}, Y_{off}, Z_{off}$ are prior known X, Y, Z components of the directional calibration parameters for the set straight line for the object; the matrix $M_S$ $$\begin{bmatrix} M_S(1,1) & M_S(1,2) & M_S(1,3) \\ M_S(2,1) & M_S(2,2) & M_S(2,3) \\ M_S(3,1) & M_S(3,2) & M_S(3,3) \end{bmatrix}$$

is the current three-dimensional rotation matrix for computing action direction.

17. A system configured to track an object, the system including a calibration tool comprising:

a chassis; and a holding bracket, wherein:

the holding bracket is disposed over the chassis and configured to hold the object, the object has at least one tracking marker disposed thereon, the holding bracket is configured to keep a direction of a straight line for the object unchanged in a three-dimensional space, while still allowing the object to rotate around the straight line as an axis;

the tracking marker is disposed in a traceable region for the system;

the system is configured to receive signal from, and deduce at least direction of, the tracking marker in the three-dimensional space;

during rotation of the object, at least two groups of rotation status parameters of the tracking marker are obtained in at least two different rotation positions, and based on the at least two groups of rotation status parameters, the system is configured to determine at least two three-dimensional rotation matrices for computing directional calibration parameters; and the system is configured to solve simultaneous equations to compute the directional calibration parameters for a set direction of the object.

18. The system according to claim 17, wherein the signal is at least one of infrared tracking signal or electromagnetic tracking signal.

19. The system of claim 17, wherein the simultaneous equations are derived from at least one of a formula of a two-point position relationship, a formula of a two-direction relationship, or a formula of a linear direction rotation relationship in the three-dimensional space.

20. The system of claim 19, wherein the simultaneous equations are solved based on at least one formula for determining a distance between two points in the three-dimensional space.

21. The system of claim 19, wherein the simultaneous equations are solved by having one of the components of the direction be a non-zero constant in the three-dimensional space.

22. The system of claim 19, wherein the derivation of the simultaneous equations from the formula of a two-point position relationship comprises:

setting point A and point B on the set straight line with a distance D apart, wherein D is a number larger than 0; setting point O on the tracking marker's center to represent the tracking marker; setting three-dimensional coordinates A $(X_A, Y_A, Z_A)$, B$(X_B, Y_B, Z_B)$ and C(Xc,Yc, Zc) respectively;

substituting the three-dimensional coordinates of point A, B, and O into the formula of a two-point position relationship in the three-dimensional space to obtain simultaneous equations 1)-9):

$$X_A = X_c + X_{AO} \times M_p(1,1) + Y_{AO} \times M_p(2,1) + Z_{AO} \times M_p(3,1) \quad 1);$$

$$Y_A = Y_c + X_{AO} \times M_p(1,2) + Y_{AO} \times M_p(2,2) + Z_{AO} \times M_p(3,2) \quad 2);$$

$$Z_A = Z_c + X_{AO} \times M_p(1,3) + Y_{AO} \times M_p(2,3) + Z_{AO} \times M_p(3,3) \quad 3);$$

$$X_B = X_c + X_{BO} \times M_p(1,1) + Y_{BO} \times M_p(2,1) + Z_{BO} \times M_p(3,1) \quad 4);$$

$$Y_B = Y_c + X_{BO} \times M_p(1,2) + Y_{BO} \times M_p(2,2) + Z_{BO} \times M_p(3,2) \quad 5);$$

$$Z_B = Z_c + X_{BO} \times M_p(1,3) + Y_{BO} \times M_p(2,3) + Z_{BO} \times M_p(3,3) \quad 6);$$

$$X_{off} = X_{AO} - X_{BO} \quad 7);$$

$$Y_{off} = Y_{AO} - Y_{BO} \quad 8);$$

$$Z_{off} = Z_{AO} - Z_{BO} \quad 9);$$

wherein $X_{AO}, Y_{AO}, Z_{AO}$ are offset distances between point A and point O; $X_{BO}, Y_{BO}, Z_{BO}$ are offset distances between point B and point O; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, . . . , n, where n is a positive integer greater than 1; $X_{off}, Y_{off}, Z_{off}$ are X, Y, Z components of the directional calibration parameters for the set straight line for the object.

23. The method of claim 19, wherein the derivation of the simultaneous equations from the formula of a linear direction rotation relationship, or from the formula of a two-direction relationship comprises:

setting $\delta x = X_A - X_B$, $\delta y = Y_A - Y_B$, $\delta z = Z_A - Z_B$, where $\delta x$, $\delta y$, $\delta z$ represent X, Y, Z components of the linear direction in three-dimensional coordinate system;

obtaining equations 10)-12) based on the formula of a linear direction rotation relationship, or the formula of a two-direction relationship:

$$\delta x = X_{off} \times M_p(1,1) + Y_{off} \times M_p(2,1) + Z_{off} \times M_p(3,1) \quad 10);$$

$$\delta y = X_{off} \times M_p(1,2) + Y_{off} \times M_p(2,2) + Z_{off} \times M_p(3,2) \quad 11);$$

$$\delta z = X_{off} \times M_p(1,3) + Y_{off} \times M_p(2,3) + Z_{off} \times M_p(3,3) \quad 12);$$

wherein $X_{off}, Y_{off}, Z_{off}$ are X, Y, Z components of the directional calibration parameters for the set straight line for the object, or are X, Y, Z components of "zero" direction; the matrix $M_p$ $$\begin{bmatrix} M_p(1,1) & M_p(1,2) & M_p(1,3) \\ M_p(2,1) & M_p(2,2) & M_p(2,3) \\ M_p(3,1) & M_p(3,2) & M_p(3,3) \end{bmatrix}$$

is the Pth matrix of three-dimensional rotation for computing the directional calibration parameters, p=1, 2, . . . , n, where n is a positive integer greater than 1.

* * * * *